(12) United States Patent
Sato

(10) Patent No.: US 8,679,021 B2
(45) Date of Patent: Mar. 25, 2014

(54) ULTRASONIC DIAGNOSTIC APPARATUS, ULTRASONIC DIAGNOSTIC METHOD AND DATA PROCESSING PROGRAM FOR ULTRASONIC DIAGNOSTIC APPARATUS

(75) Inventor: Takeshi Sato, Tochigi-Ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 635 days.

(21) Appl. No.: 12/521,815

(22) PCT Filed: Jan. 29, 2009

(86) PCT No.: PCT/JP2009/051501
§ 371 (c)(1),
(2), (4) Date: Jun. 30, 2009

(87) PCT Pub. No.: WO2009/110268
PCT Pub. Date: Sep. 11, 2009

(65) Prior Publication Data
US 2010/0324424 A1    Dec. 23, 2010

(30) Foreign Application Priority Data

Mar. 3, 2008  (JP) ................................. 2008-052261

(51) Int. Cl.
*A61B 8/00* (2006.01)

(52) U.S. Cl.
USPC ........... 600/453; 600/454; 600/455; 600/456; 600/457

(58) Field of Classification Search
USPC ................................................ 600/453–457
See application file for complete search history.

(56) References Cited

U.S. PATENT DOCUMENTS

| | | | | |
|---|---|---|---|---|
| 5,107,466 | A | * | 4/1992 | Nishiyama et al. ............. 367/90 |
| 5,109,858 | A | * | 5/1992 | Nishiyama et al. ........... 600/455 |
| 2006/0064012 | A1 | * | 3/2006 | Waag et al. ................... 600/437 |
| 2007/0066896 | A1 | | 3/2007 | Simopoulos et al. | |

OTHER PUBLICATIONS

Naohiro Yamada, et al., "Comparison of InSAR phase Unwrapping algorithms by using DEM", Proceedings of the Japanese Conference on Remote Sensing, pp. 15 and 16, (Nov. 27, 1997) (with English abstract).

International Preliminary Report on Patentability issued Oct. 12, 2010 in International Application No. PCT/JP2009/051501.

Office Action issued Jan. 22, 2013, in Japanese Patent Application No. 2008-052261, filed Mar. 3, 2008 (with English-language translation).

Naohiro Yamada et al, "Comparison of InSAR Phase Unwrapping Algorithms by Using DEM", Proceedings of the 23$^{rd}$ Autumn Conference of the Remote Sensing Society of Japan, Nov. 27, 1997, pp. 15-16.

Go Oishi, "Four Reference-Point Method: A Compensation Method of the Distortion Caused by Global Transform Phase Unwrapping", Master's Thesis (Division of Transdisciplinary Sciences, Department of Frontier Informatics), Univ. of Tokyo, Mar. 2005, pp. 5-16.

* cited by examiner

*Primary Examiner* — Unsu Jung
*Assistant Examiner* — Joseph M Santos Rodriguez
(74) *Attorney, Agent, or Firm* — Oblon, Spivak, McClelland, Maier & Neustadt, L.L.P.

(57) ABSTRACT

An ultrasonic diagnostic apparatus includes a data acquisition unit, a correction unit and a display unit. The data acquisition unit acquires phase signals as Doppler data from a moving object in an object by transmitting and receiving ultrasonic waves to and from the object. The correction unit performs global aliasing correction processing of the phase signals based on a continuity in a two-dimensionally phase change. The display unit displays phase signals after the aliasing correction processing.

7 Claims, 5 Drawing Sheets

ULTRASONIC DIAGNOSTIC APPARATUS, ULTRASONIC DIAGNOSTIC METHOD AND DATA PROCESSING PROGRAM FOR ULTRASONIC DIAGNOSTIC APPARATUS

BACKGROUND OF THE INVENTION

1. Field of the Invention

The present invention relates to an ultrasonic diagnostic apparatus, an ultrasonic diagnostic method and a data processing program for ultrasonic diagnostic apparatus that generate and display a B mode image which is tissue information of an object and a color Doppler image which is motion information of blood and tissues by transmission and reception of ultrasonic waves, and more particularly, to an ultrasonic diagnostic apparatus, an ultrasonic diagnostic method and a data processing program for ultrasonic diagnostic apparatus that correct aliasing of velocities in a color Doppler image.

2. Description of the Related Art

The color Doppler method in ultrasonic diagnosis is a method to irradiate ultrasonic waves in a living body in the same direction plural times and to extract blood flow information such as a velocity, a power and a dispersion of blood flow by Doppler effect.

In the color Doppler method, signals corresponding to slow-moving from tissues are suppressed by firstly applying a high pass filter (HPF) called a moving target indication (MTI) filter to plural ultrasonic reception signals from the same point. Note that, in the case of observing a moving velocity of not a blood flow but a tissue, the MTI filter is not necessary. Next, the reception signals passing through the MTI filter are applied to an autocorrelator. Then, a power, a dispersion and a velocity of a moving object such as a blood flow and the like are calculated from the output signals of the autocorrelator.

Here, when the velocity exceeds the aliasing velocity, aliasing phenomenon occurs. This derives from the fact that the phase obtained for calculation of a power, a dispersion and a velocity can become only a value in the range of $-\pi$ to $+\pi$. That is, when the velocity exceeds the aliasing velocity, the phase is folded from $+\pi$ to $-\pi$. This is a limit under the sampling theorem. In a color Doppler image, colors change when the velocity exceeds the aliasing velocity. Therefore, there is a possibility that the observation becomes difficult and diagnosis of a blood flow direction is failed.

The conventional color Doppler ultrasonic diagnostic apparatus has a function called zero shift. The function changes the phase range of $-\pi$ to $+\pi$ into the phase range of 0 to $+2\pi$. This allows observing a blood flow velocity in a direction toward an ultrasonic beam up to twice the aliasing velocity. However, the function can be used only under the condition of no blood flow in a direction away from an ultrasonic beam. That is to say, even if the zero shift is performed, an observable velocity range is $2\pi$.

A staggered pulse method is a method to measure a phase exceeding $2\pi$ which is a limit under the sampling theorem (for example, refer to the patent documents 1, 2 and 3). The staggered pulse method is put to practical use in the field of radar, however, still not in the field of ultrasonic diagnostic apparatus. The reason is that phase interference called speckle occurs in an ultrasonic reflection echo and a second-order subtraction of a phase cannot be observed stably.

Further, the technology to expand a velocity dynamic range (an aliasing velocity/a detectable low flow velocity) with keeping a phase detection range $2\pi$ by improving low flow velocity detectability is devised (for example, refer to the patent document 4). However, this technology is not to increase an aliasing velocity.

On the other hand, there is unwrap as a method to detect a phase exceeding $2\pi$, by assuming a continuity of phase change.

FIG. 1 is a diagram explaining unwrap processing in the conventional ultrasonic diagnostic apparatus.

In (a) and (b) of FIG. 1, each abscissa denotes a position and each ordinate axis denotes a phase of signal.

The unwrap is a method in which an occurrence of an aliasing is recognized in case where a phase of the current point is a positive phase and a phase of the adjacent point is a negative phase so that a difference between both the phases is approximate $2\pi$, and a value derived by adding $2\pi$ to the phase of the adjacent point is regarded as a new phase value of the adjacent point.

Therefore, as shown in FIG. 1 (a), the observed signals of which phases are folded in the range of $-\pi$ to $+\pi$ are corrected to signals having a continuity as shown in FIG. 1 (b) by unwrap processing.

However, the unwrap processing can be performed only as one-dimensional processing basically. Therefore, when the unwrap processing is performed on the line in the interval direction, points to which wrong aliasing correction is performed due to a noise may appear. As mentioned above, when wrong aliasing correction is performed, the phase sifts by $2\pi$ from each point to which the wrong aliasing correction is performed. For this reason, a two-dimensional image like with codes may be generated.

The method to perform local unwrap processing two-dimensionally using a two-dimensional velocity distribution is devised as a measure to the problem as mentioned above (for example, refer to the patent document 5). The method to perform a local unwrap processing is a method to define points, on each of which a round integration value of gradient of a phase is not 0, containing a point in a two-dimensional space, as residues and to select a route so that the residues are avoided.

However, the conventional method to perform the local unwrap processing two-dimensionally has a problem that it takes a long time to calculate for a complicated processing. Further, there is a problem that the points to avoid the residues become image to be visible awkwardly in the case where the number of the residues is many. Additionally, there is a problem that unwrap may become impossible due to a robustness problem.

[Patent Document 1]
Japanese Publication of Patent Application No. 4-197249
[Patent Document 2]
Japanese Publication of Patent Application No. 4-197250
[Patent Document 3]
Japanese Publication of Patent Application No. 4-278864
[Patent Document 4]
Japanese Publication of Patent Application No. 2005-176997
[Patent Document 5]
United States Patent Application Publication No. US 2007/0066896

SUMMARY OF THE INVENTION

The present invention has been made in light of the conventional situations, and it is an object of the present invention to provide an ultrasonic diagnostic apparatus, an ultrasonic diagnostic method and a data processing program for ultrasonic diagnostic apparatus which make it possible to perform aliasing correction of acquired velocity data more satisfactorily and stably by reducing influence of noise in imaging under the color Doppler method.

The present invention provides an ultrasonic diagnostic apparatus comprising: a data acquisition unit configured to acquire phase signals as Doppler data from a moving object in an object by transmitting and receiving ultrasonic waves to and from the object; a correction unit configured to perform global aliasing correction processing of the phase signals based on a continuity in a two-dimensionally phase change; and a display unit configured to display phase signals after the aliasing correction processing, in an aspect to achieve the object.

The present invention also provides an ultrasonic diagnostic method comprising: acquiring phase signals as Doppler data from a moving object in an object by transmitting and receiving ultrasonic waves to and from the object; performing global aliasing correction processing of the phase signals based on a continuity in a two-dimensionally phase change; and displaying phase signals after the aliasing correction processing, in an aspect to achieve the object.

The present invention also provides a data processing program, for ultrasonic diagnostic apparatus, causing a computer to function as: a correction unit configured to acquire phase signals acquired from a moving object in an object by transmitting and receiving ultrasonic waves to and from the object and perform global aliasing correction processing of the phase signals based on a continuity in a two-dimensionally phase change; and an image data generating unit configured to generate image data for displaying using phase signals after the aliasing correction processing, in an aspect to achieve the object.

The ultrasonic diagnostic apparatus, the ultrasonic diagnostic method and the data processing program for ultrasonic diagnostic apparatus as described above make it possible to perform aliasing correction of acquired velocity data more satisfactorily and stably by reducing influence of noise in imaging under the color Doppler method.

BRIEF DESCRIPTION OF THE DRAWINGS

In the accompanying drawings.

DESCRIPTION OF THE PREFERRED EMBODIMENTS

An ultrasonic diagnostic apparatus, an ultrasonic diagnostic method and a data processing program for ultrasonic diagnostic apparatus according to embodiments of the present invention will be described with reference to the accompanying drawings.

(Configuration and Function)

Figure 1:
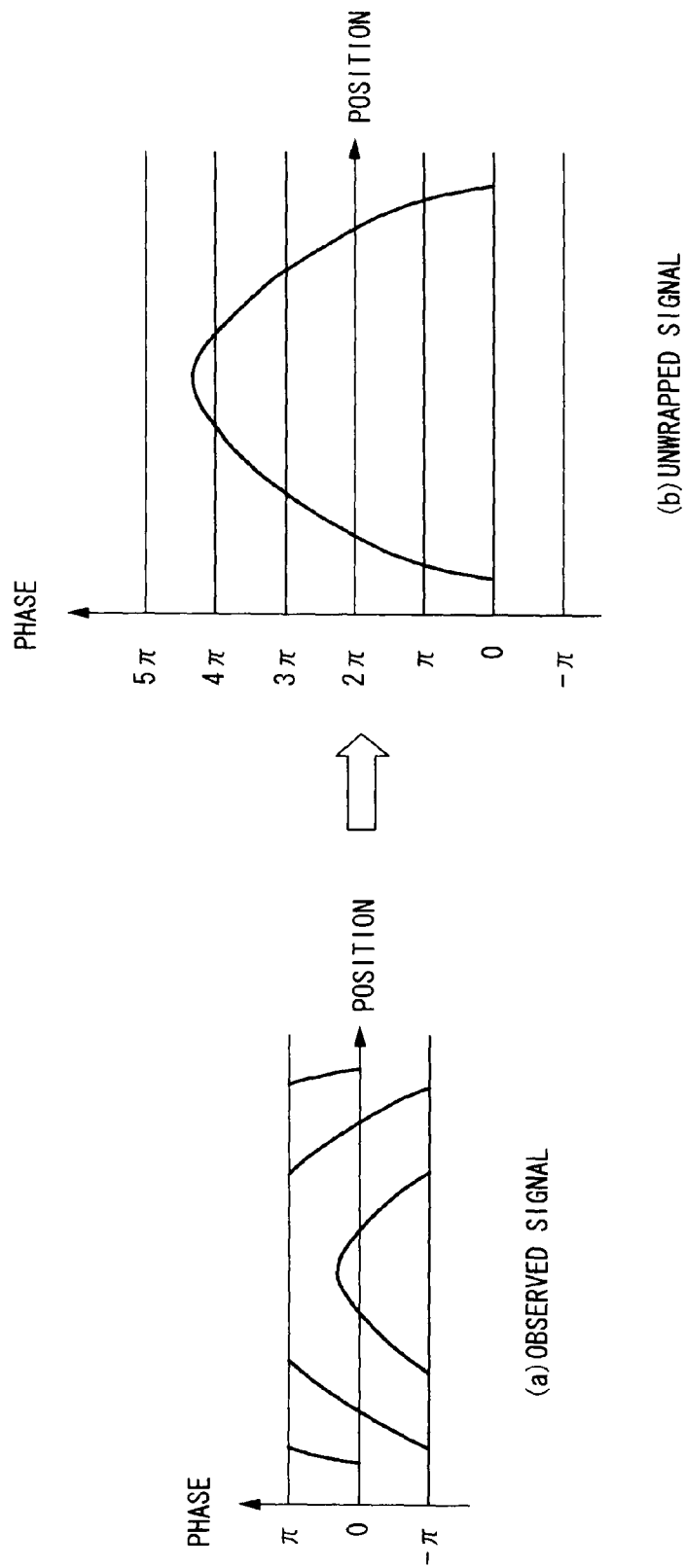
FIG. 1 is a diagram explaining unwrap processing in the conventional ultrasonic diagnostic apparatus.
Figure 2:
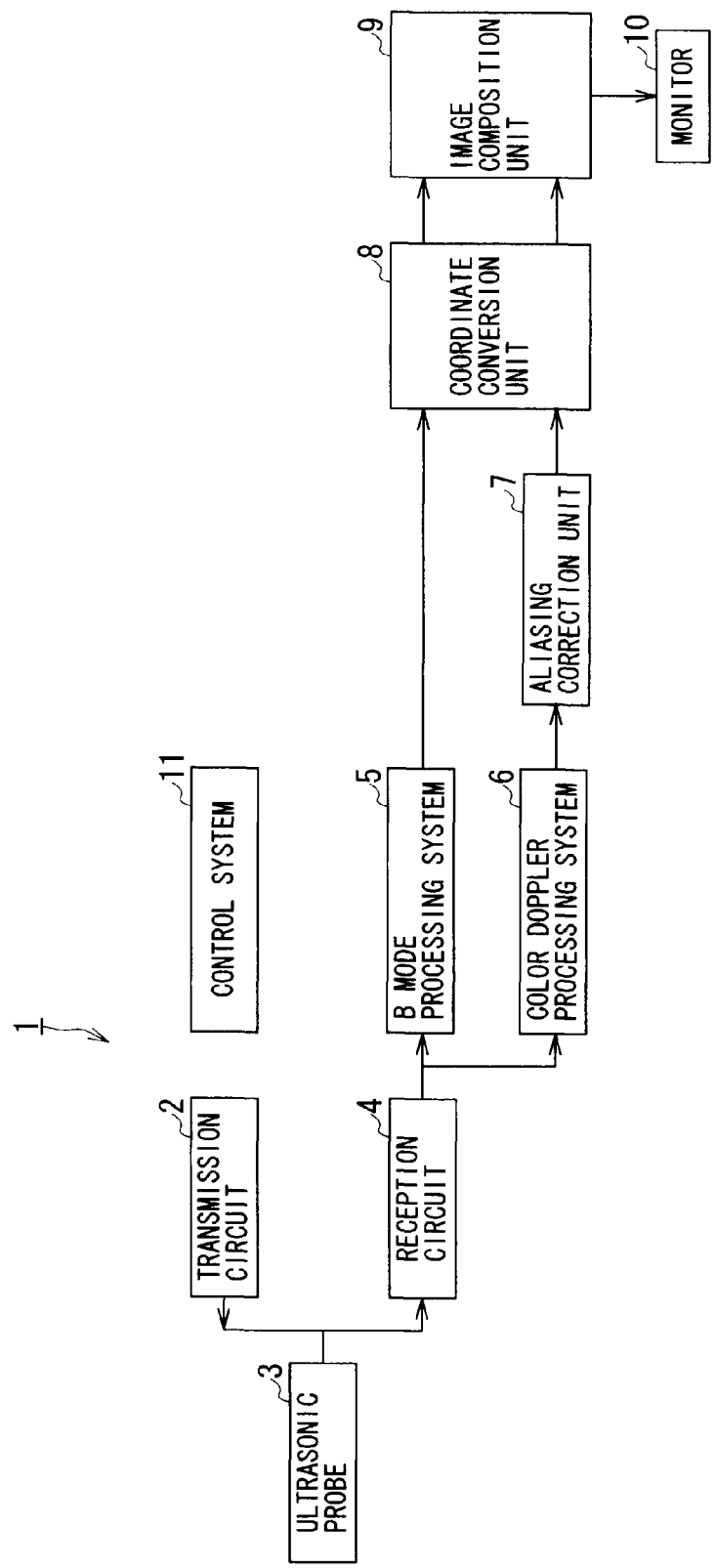
FIG. 2 is a block diagram showing an ultrasonic diagnostic apparatus according to an embodiment of the present invention.

FIG. 2 is a block diagram showing an ultrasonic diagnostic apparatus according to an embodiment of the present invention.

The ultrasonic diagnostic apparatus 1 is a color Doppler ultrasonic diagnostic apparatus configured to measure a moving velocity of a moving object such as red blood cells and a tissue moving in an object like a living body by transmission and reception of ultrasonic waves to and from the object with using a phase shift and to display the measured two-dimensional velocity distribution of the object.

For that purpose, the ultrasonic diagnostic apparatus 1 includes a transmission circuit 2, an ultrasonic probe 3, a reception circuit 4, a B mode processing system 5, a color Doppler processing system 6, an aliasing correction unit 7, a coordinate conversion unit 8, an image composition unit 9, a monitor 10 and a control system 11. Each element of the ultrasonic diagnostic apparatus 1 can be configured by a circuit or a computer into which program is read. For example, a data processing system which generates image data using pieces of data output from the B mode processing system 5 and the color Doppler processing system 6 as pieces of processing target data respectively by reading a data processing program of an ultrasonic diagnostic apparatus into a computer is put to practical use. In this case, the aliasing correction unit 7, the coordinate conversion unit 8 and the image composition unit 9 are configured by the computer into which a data processing program is read.

The transmission circuit 2 has a function to apply transmission signals to the ultrasonic probe 3. The ultrasonic probe 3 has plural ultrasonic transducers. The ultrasonic probe 3 has a function to convert the transmission signals applied from the transmission circuit 2 into ultrasonic signals using the respective ultrasonic transducers to transmit the ultrasonic signals to an object not shown in the figure. In addition, the ultrasonic probe 3 has a function to receive ultrasonic reflected signals which is generated in an object to convert the received ultrasonic reflected signals into reception signals and to output the reception signals to the reception circuit 4. The reception circuit 4 has a function to perform a required signal processing including a phasing-and-adding processing of the reception signals obtained from the ultrasonic probe 3 and to output a reception signal for generating a B mode image to the B mode processing system 5, meanwhile, to output a reception signal for generating a color Doppler image displaying a two-dimensional blood flow velocity to the color Doppler processing system 6. The B mode processing system 5 has a function to generate B mode image data by performing a B mode image generation processing of the reception signal for generating the B mode image obtained from the reception circuit 4 and to output the generated B mode image data to the coordinate conversion unit 8.

The color Doppler processing system 6 has a function to generate color Doppler image data including velocity signals, phase signals, powers signal and dispersion signals of a moving component such as a blood flow by a color-Doppler-image-generation processing of the reception signals for generating a color Doppler image obtained from the reception circuit 4 and to output the generated color Doppler image data to the aliasing correction unit 7.

The color Doppler processing system 6 includes a HPF called a MTI filter, an autocorrelator and a velocity/dispersion/power calculator. Note that, in the case of observing a moving velocity of not a blood flow but a tissue, the MTI filter is not necessary. The MTI filter of the color Doppler processing system 6 has a function to suppress slow-moving signals from a tissue by applying the HPF with the reception signals for generating a color Doppler image obtained from the reception circuit 4 and to extract moving signals which are reception signals from moving components. The autocorrelator of the color Doppler processing system 6 has a function to calculate intermediate signals for calculating power signals P, dispersion signals T, velocity signals V and phase signals φ of moving component such as a blood flow as color Doppler image data based on the moving signals extracted by the MTI filter.

The autocorrelator performs the processing as shown in equation (1-1) and equation (1-2). That is, when an output signal train of the MTI filter is denoted by x(1), x(2), x(3), ..., x(n), signals c0, c1 are output from the autocorrelator. Note that, * represents the complex conjugate number in equation (1-1) and equation (1-2).

$$c0 = \frac{1}{n}\sum_{k=1}^{n} x^*(k)x(k) \quad (1\text{-}1)$$

$$c1 = \frac{1}{n-1}\sum_{k=1}^{n-1} x^*(k)x(k+1) \quad (1\text{-}2)$$

The velocity/dispersion/power calculator of the color Doppler processing system 6 has a function to calculate a power signal P, a dispersion signal T, a velocity signal V and a phase signal φ of moving component with equation (2-1), equation (2-2), equation (2-3), equation (2-4) and equation (2-5). Note that, m, C, PRF, f0, Re ( ) Im ( ) and atan 2 ( ) denote a reference value, a sound velocity, a pulse repetition frequency in a same direction, a reception frequency, a function for extracting the real part, a function for extracting the imaginary part and a function for calculating an angle from −π to +π respectively.

$$P = 10\log_{10}(c0/m) \quad (2\text{-}1)$$

$$T = 1 - \frac{|c1|}{c0} \quad (2\text{-}2)$$

$$V = V_{Nyq} \cdot \frac{\phi}{\pi} \quad (2\text{-}3)$$

wherein $$\phi = \text{atan }2(Im(c1), Re(c1)) \quad (2\text{-}4)$$

$$V_{Nyq} = \frac{C \cdot PRF}{4f_0} \quad (2\text{-}5)$$

When the velocity signal V shown in equation (2-3) exceeds a fold velocity $V_{Nyq}$, aliasing is produced.

For that reason, the aliasing correction unit 7 has a function to obtain color Doppler image data from the color Doppler processing system 6, to perform aliasing correction by a global, i.e. not local, unwrapping processing of the phase signal φ calculated with equation (2-4) based on a continuity of two-dimensional phase variation and to output the color Doppler image data after aliasing correction processing to the coordinate conversion unit 8.

Note that, the word "velocity" is often used as information displayed as a color Doppler image generally. However, a "velocity" is expressed by equation (2-3) precisely and the information displayed as a color Doppler image is generally a "phase" expressed by equation (2-4). Therefore, the information displayed as a color Doppler image is explained as a "phase" here.

The function equipped in the aliasing correction unit 7 can be realized by a software processing with reading a program into a devise such as a CPU (Central Processing Unit), a DSP (Digital Signal Processor) or a GPU (Graphics Processing Unit), a processing with a hardware like a circuit using an ASIC (Application Specific Integrated Circuit), a FPGA (Field Programmable Gate Array) or an Integrated Circuit or a processing combining the software processing with the hardware processing.

Specifically, the aliasing correction unit 7 has a function to perform a processing to calculate phase signals Θ [i, j] without aliasing from phase signals φ [i, j] with aliasing according to the following procedure.

Figure 3:
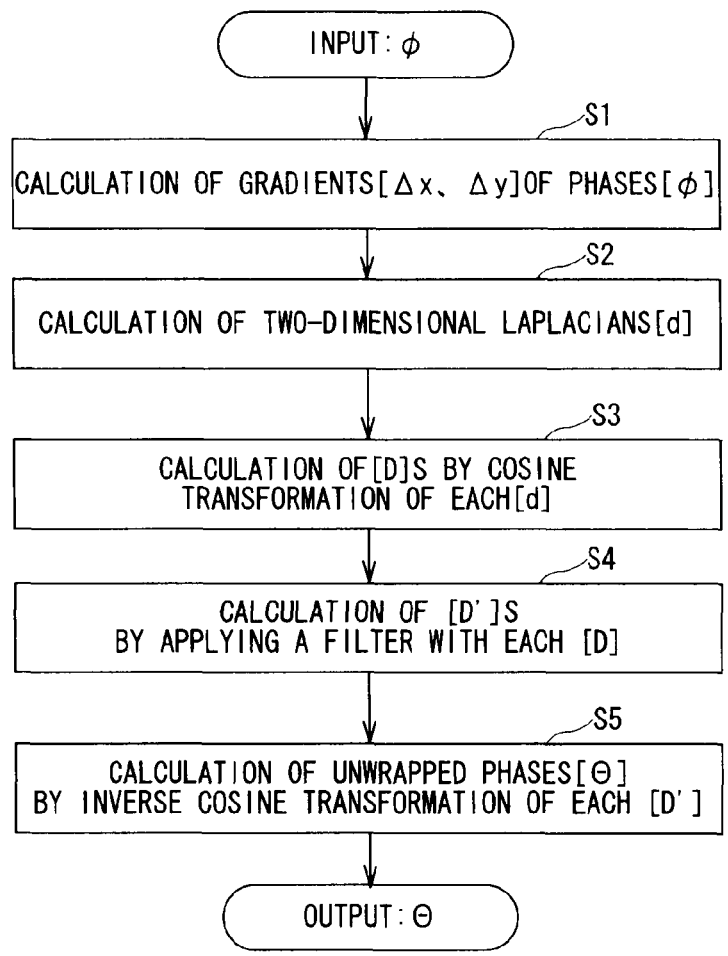
FIG. 3 is a flowchart showing an example of procedure for aliasing correction processing of phase signals in the aliasing correction unit shown in FIG. 2.

FIG. 3 is a flowchart showing an example of procedure for aliasing correction processing of phase signals in the aliasing correction unit 7 shown in FIG. 2. Reference numerals each having a number added to reference symbol S denote steps in the flowchart shown in FIG. 3.

First, in step S1, the phase signals φ [i, j] calculated with equation (2-4) by observing is to be input signals, and a gradient Δx[i, j] of the phase signals φ [i, j] in the x direction and a gradient Δy[i, j] of the phase signals φ [i, j] in the y direction are calculated with equation (3). Note that, in equation (3), W(φ) is a wrap function which folds phase signals φ in the range of −π to +π. Here, a processing for folding a phase in the range of −π to +π is called wrap.

$$\Delta x[i, j] = \quad (3)$$
$$\begin{cases} W(\phi[i+1, j] - \phi[i, j]), & (0 \le i \le M-2 \;\; 0 \le j \le N-1) \\ 0, & \text{otherwise} \end{cases}$$

$$\Delta y[i, j] = \begin{cases} W(\phi[i, j+1] - \phi[i, j]), & (0 \le i \le M-1 \;\; 0 \le j \le N-2) \\ 0, & \text{otherwise} \end{cases}$$

Next, in step S2, two-dimensional Laplacians d[i, j] are calculated from the gradient Δx[i, j] of the phase signals φ [i, j] in the x direction and the gradient Δy[i, j] of the phase signals φ [i, j] in the y direction by equation (4).

$$d[i,j] = (\Delta x[i,j] - \Delta x[i-1,j]) + (\Delta y[i,j] - \Delta y[i,j-1]) \quad (4)$$

Next, in step S3, as shown in equation (5), D[k, p] are calculated by a two-dimensional discrete cosine transformation of the two-dimensional Laplacians d[i, j].

$$D[k, p] = \sum_{i=0}^{M-1}\sum_{j=0}^{N-1} 4d[i, j]\cos\left\{\frac{\pi}{2M}k(2i+1)\right\}\cos\left\{\frac{\pi}{2N}p(2j+1)\right\} \quad (5)$$

Next, in step S4, D′[k, p] are calculated by applying a filter with the D[k, p] using a calculation shown in equation (6).

$$D'[k, p] = \frac{D[k, p]}{2\left(\cos\frac{\pi k}{M} + \cos\frac{\pi p}{N} - 2\right)} \quad (6)$$

Next, in step S5, as shown in equation (7), unwrapped phase signals Θ [i, j] can be calculated as output signals by a two-dimensional discrete inverse cosine transformation of the D'[k, p]. Note that, here, a processing for restoring phase signals Φ wrapped in the range of −π to +π to original phase signals Θ is called unwrap.

$$\Theta[i, j] = \frac{1}{MN} \sum_{k=0}^{M-1} \sum_{p=0}^{N-1} w_1(k) w_2(p) D'[k, p] \cos\left\{\frac{\pi}{2M} k(2i+1)\right\} \cos\left\{\frac{\pi}{2N} p(2j+1)\right\} \quad (7)$$

wherein $w_1(k) = \begin{cases} 1/2, & (m=0) \\ 1, & (m \geq 1) \end{cases}$  $w_2(p) = \begin{cases} 1/2, & (p=0) \\ 1, & (p \geq 1) \end{cases}$ Next, effect by the above-mentioned processing will be described.

Figure 4:
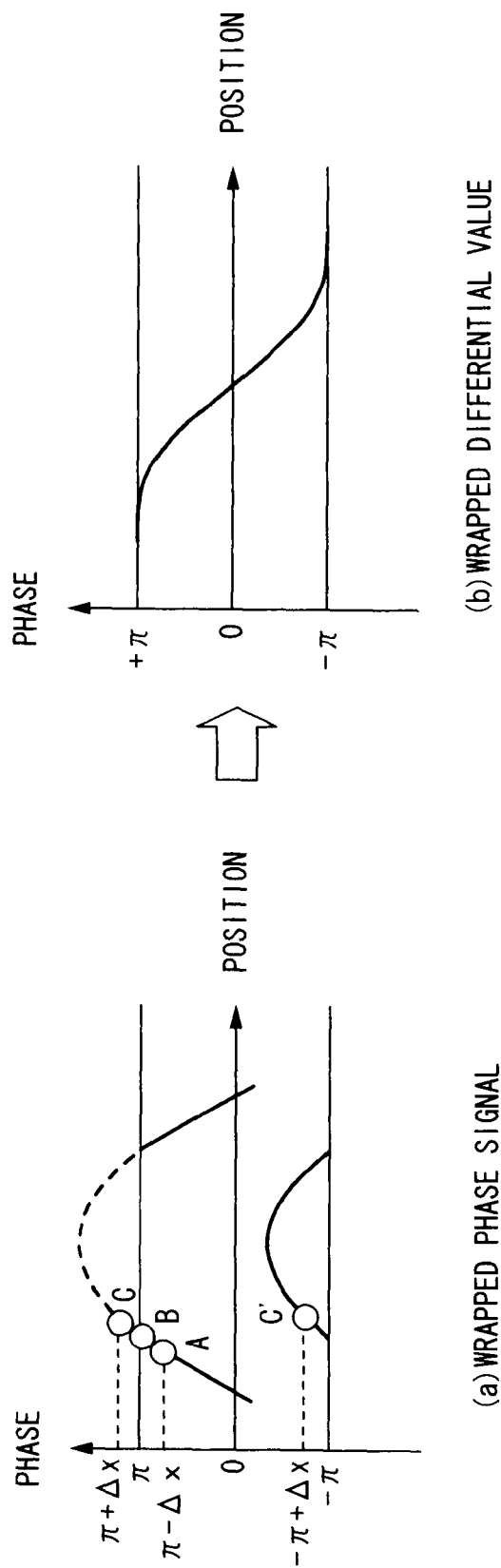
FIG. 4 is a diagram explaining the principle of aliasing correction processing of the phase signals in the aliasing correction unit shown in FIG. 2.

FIG. 4 is a diagram explaining the principle of aliasing correction processing of the phase signals in the aliasing correction unit 7 shown in FIG. 2.

In (a) and (b) of FIG. 4, each abscissa axis denotes position and each ordinate axis denotes phase. FIG. 4 (a) shows the wrapped phase signals φ having an aliasing and FIG. 4 (b) shows signals derived by wrapping the spatially differentiation result of the wrapped phase signals φ shown in FIG. 4 (a) into a range of −π to +π.

As shown in FIG. 4 (a), when a phase of data A is π−Δx, a phase of data B is π and a phase of data C is π+Δx, the data C is folded to data C' having a phase of −π+Δx. As mentioned above, even if an aliasing is generated in the observed phase signals φ, the values obtained by wrapping the result of differentiating the phase signals φ with regard to space in the range of −π to +π are equal to the values obtained by differentiating the unwrapped phase signals Θ without an aliasing with regard to space, as shown in FIG. 4 (b).

That is, as shown in equation (8), a wrap value W(Δφ) of difference value Δφ between the phase π of data B observed practically and the phase −π+Δx of folded data C' by the wrap function W becomes Δx.

$$W(\Delta\phi) = W\{(-\pi+\Delta x)-\pi\} = W(-2\pi+\Delta x) = \Delta x \quad (8)$$

It is found that the wrap value W(Δφ) difference value Δφ between the phase π of data B observed practically and the phase −π+Δx of folded data C' by the wrap function W is equal to the difference value between the phase π of data B observed practically and the phase π+Δx of data C from equation (8).

For that reason, as shown in equation (3), spatial differences of the wrapped phase signals φ [i, j] are calculated. Equation (4) represents the spatial Laplacians. Then, Poisson equation which is expressed in a partial differential equation shown in equation (9) is established.

$$\frac{\partial^2 \Theta}{\partial x^2} + \frac{\partial^2 \Theta}{\partial y^2} = d \quad (9)$$

From equation (9), To calculate a distribution of the true unwrapped phase signals Θ comes down to resolve Neumann's boundary condition in a discrete Poisson equation. The solution methods thereof include a speed-up technique by a spectrum method. The speed-up technique by the spectrum method corresponds to processing of step S3, step S4 and step S5 in FIG. 3 described above.

An effect to perform integration can be obtained on the spatial axis by a filter operation on the frequency axis shown as the division by the denominator shown in equation (6).

Therefore, when an inverse cosine transformation shown in equation (7) is performed to the signals after the division processing of equation (6), unwrapped phase signals Θ can be calculated.

The above described aliasing correction (unwrap) processing by a method of least squares minimizing square errors between data obtained by folding the gradients Δx, Δy of two-dimensional distribution of the phase signals φ and the gradients of two-dimensional distribution of the phase signals Θ after the aliasing correction processing becomes a processing for unwrapping not locally but globally. Therefore, by the unwrap processing shown in FIG. 3, the phase signals Θ optimized in the whole of space are output so that each square error becomes minimum.

Note that, the spectrum method as a solution method of the partial differential equation as shown by equation (9) includes a method with using a discrete Fourier transform and a discrete inverse Fourier transform and a method with using a discrete sine transform and a discrete inverse sine transform other than the method described above. Therefore, the unwrapped phase signals Θ may be obtained with each of the methods mentioned above.

Though the unwrap processing of the phase signals φ to calculate the unwrapped phase signals Θ by equation (3) to equation (7) described above is calculation processing with setting weights of the phase signals φ in respective points in the observed phase signal distribution as equal, it can be also performed with arbitrary weights. The unwrap processing by a weighted least squares method which adds weighting to a calculation under a least squares method can be performed according to the following procedure.

Suppose the phase vector after unwrapping is θ having a size MN, the difference value vector of the observed phase signals φ is b having a size 2 MN, the Laplacian matrix is $P=A^T A$ using the matrix A having 2 MN rows and MN columns and the weighting matrix is W having 2 MN rows and 2 MN columns, then equation (10) can be yielded.

$$A^T W^T W A \theta = A^T W^T W b \quad (10)$$

The equation (10) cannot be solved directly, however, can be solved by calculating equation (11) repeatedly.

$$P\theta_{k+1} = A^T W^T W b - (A^T W^T W A - A^T A) \theta_k \quad (11)$$

Note that, the difference value vector b of the observed phase signals φ in equation (11) is equivalent to a one-dimensional vector in equation (3) in which the gradients Δx in the x direction or the gradients Δy in the y direction of the phase signals φ are arranged. Therefore, the size of the difference value vector b becomes 2 MN and the difference value vector b can be calculated by equation (12).

$$b(k) = \begin{cases} \Delta x[i, j], & i = \mod(k, M), j = \text{floor}(k/N), \\ & 0 \leq k < MN \\ \Delta y[i, j], & i = \mod(k, M), j = \text{floor}((k-MN)/N), \\ & MN \leq k < 2MN \end{cases} \quad (12)$$

In equation (11), the weighting matrix W is weights to respective elements of the difference value vector b of the observed phase signals φ. Therefore, the weighting matrix W becomes a matrix having 2 MN rows and 2 MN columns. The respective elements of the weighting matrix W can be set to desired values by an arbitrary method, depending on a condition of data to be a weighting target.

For example, the values of the weighting matrix W can be set using the power signals P calculated by equation (2-1). Generally, an observed phase signal φ are highly likely to be affected by a noise when a value of the power signal P is low. Then, a value of the weighting matrix W is set so as to be lower at a position where a value of the power signal P is lower. That is, a weight of a phase signal φ corresponding to a small power signal P value can be set low relatively so that an influence that each phase signal φ corresponding to the small power signal P value gives to the unwrap processing is reduced. By setting the weight of data on each position which has a high possibility of being affected by noise to be low relatively, the influence of a noise can be reduced.

In case where the weighting matrix W is determined depending on a value of the power signal P, a threshold Pth is set to the power signal P. Then, the weighting matrix W is to be a diagonal matrix and values of respective elements other than the on-diagonal elements are set to be 0. The value W[k] of the k-th on-diagonal element of the weighting matrix W can be determined as equation (13) with the threshold Pth of the power signal P.

$$W[k] = \begin{cases} 1, & P[i,j] \geq Pth \\ Q(P[i,j]), & \text{otherwise} \end{cases} \quad (13)$$

wherein $$[i,j] = \begin{cases} i = \mod(k, M), j = \text{floor}(k/N), & 0 \leq k < MN \\ i = \mod(k, M), j = \text{floor}((k-MN)/N), & MN \leq k < 2MN \end{cases}$$

In equation (13), $0 \leq Q(p) \leq 1$, $Q(p)$ is a function having an arbitrary monotone increasing curve. When the weighting matrix W is determined as equation (13), the weighting matrix W becomes a matrix in which the weight for each power signal P not less than the threshold Pth is 1 while the weight coefficient for each power signal P less than the threshold Pth is set to be a small value depending on a value of the power signal P.

Meanwhile, since a phase signal φ also has a possibility of receiving an influence of a noise when the gradients Δx and Δy in the x direction and in the y direction of the phase signal φ in equation (3) are large, it is preferable for noise reduction that the value of the weighting matrix W to data at the corresponding position is set small. In addition, since a phase signal φ also may be influenced of a noise respectively when the dispersion signal T in equation (2-2) is large and when the velocity signal V in equation (2-3) is small, it is preferable for noise reduction that the value of the weighting matrix W to corresponding data is set small.

As mentioned above, the values of the weighting matrix W can be set with changing arbitrarily according to the gradients Δx in the x direction and the gradients Δy in the y direction of the phase signals φ, the power signals P, the dispersion signals T, the velocity signals V and other parameters representing information of a moving object. In the case of a multidimensional input to determine the values of the weighting matrix W with inputting plural parameters, for example, the values of the weighting matrix W can be determined as equation (14).

$$W[k] = \text{func}(P[i,j], \Theta[i,j], T[i,j], \Delta x[i,j], \Delta y[i,j]) \quad (14)$$

Note that, in equation (14), func( ) is a function that takes a value from 0 to 1. The function func( ) is a function having a property that the value of the function func( ) becomes small qualitatively in the cases of the small power signal P, the small unwrapped phase signal Θ, the large dispersion signal T, the large gradient Δx in the x direction of the phase signal φ and the large gradient Δy in the y direction of the phase signal φ respectively. Note that, the function func( ) does not take a small value necessarily in case where plural parameters out of the respective parameters described above change in relation to each other.

Then, the phase signals Θ, the power signals P and the dispersion signals T subjected to aliasing correction by the unwrap processing described above are output to the coordinate conversion unit 8 from the aliasing correction unit 7.

The coordinate conversion unit 8 has a function to perform coordinate conversion of the data axes of the color Doppler image data such as the phase signals Θ, the power signals P and the dispersion signals T after aliasing correction obtained from the aliasing correction unit 7 and the B mode image data obtained from the B mode processing system 5 to the orthogonal axes for image-displaying from the scan axes.

The image composition unit 9 has a function to generate image composition signals for displaying a color Doppler image overlaid with a B mode image by obtaining the color Doppler image data after aliasing correction and the B mode image data, converted into orthogonal coordinate system, from the coordinate conversion unit 8 and composing one with the other, and to display a composition image of the color Doppler image and the B mode image on the monitor 10 by providing the generated image composition signals to the monitor 10.

The control system 11 is a circuit to overall-control respective elements in the ultrasonic diagnostic apparatus 1.

(Operation and Action)

Next, the operation and action of the ultrasonic diagnostic apparatus 1 will be described.

Firstly, the transmission signals from the transmission circuit 2 are applied to the respective ultrasonic transducers of the ultrasonic probe 3. The transmission signals which are electric signals are converted into ultrasonic signals respectively in respective ultrasonic transducers. The respective ultrasonic transducers transmit the ultrasonic signals to an object respectively. Consequently, the ultrasonic reflected signals generated in the object are received by the respective ultrasonic transducers. The received ultrasonic reflected signals are converted into the reception signals which are electric signals and output to the reception circuit 4. Then, the reception circuit 4 performs necessary signal processing such as phasing-and-adding processing of the reception signals and outputs the reception signals for generating a B mode image to the B mode processing system 5, on the other hand, outputs the reception signals for generating a color Doppler image to the color Doppler processing system 6.

Therefore, B mode image data generation processing is performed to the reception signals for generating a B mode image in the B mode processing system 5 and the generated B mode image data is output to the coordinate conversion unit 8.

Meanwhile, in the color Doppler processing system 6, the HPF is applied to the reception signals for generating a color Doppler image by the MTI filter. Consequently, the slow-moving signals from tissues are suppressed and the motion signals are extracted. Next, the autocorrelator of the color Doppler processing system 6 calculates intermediate signals c0 and c1 by the calculation processing, shown in equation (1-1) and equation (1-2), of the motion signals. Next, the velocity/dispersion/power calculator of the color Doppler processing system 6 calculates the power signals P, the dispersion signals T, the velocity signals V and the phase signals φ of moving components by equation (2-1), equation (2-2), equation (2-3), equation (2-4) and equation (2-5).

Next, the color Doppler image data including the power signals P, the dispersion signals T, the velocity signals V and the phase signals φ is output to the aliasing correction unit 7. Then, the aliasing correction unit 7 performs aliasing correction by global unwrapping processing of the phase signals φ by the method described above. Then, the color Doppler image data including the aliasing-corrected phase signals Θ after unwrapping processing is output to the coordinate conversion unit 8.

Next, the coordinate conversion unit 8 converts data axes of the color Doppler image data such as the phase signals Θ, the power signals P and the dispersion signals T after the aliasing correction obtained from the aliasing correction unit 7 and the B mode image data obtained from the B mode processing system 5 to the orthogonal axes for displaying images from the scan axes. Next, the image composition unit 9 generates image composition signals for displaying a color Doppler image overlaid with a B mode image by obtaining the color Doppler image data after the aliasing correction and the B mode image data, converted into the data in the orthogonal coordinate system, from the coordinate conversion unit 8 and composing one with the other. The generated image composition signals are provided to the monitor 10 and a composition image on which the color Doppler image is overlaid with the B mode image is displayed on the monitor 10.

Figure 5:
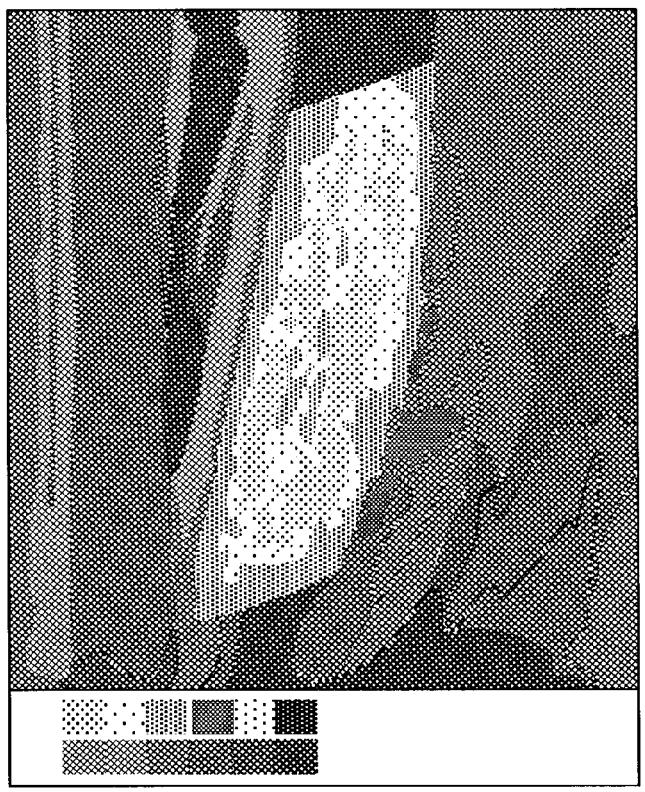
FIG. 5 is a set of images for comparing a color Doppler image generated based on the phase signals after the aliasing correction by the ultrasonic diagnostic apparatus shown in FIG. 2 with a color Doppler image generated based on the phase signals before the aliasing correction.
Figure 5:

FIG. 5 is a set of images for comparing a color Doppler image generated based on the phase signals after the aliasing correction by the ultrasonic diagnostic apparatus 1 shown in FIG. 2 with a color Doppler image generated based on the phase signals before the aliasing correction.

FIG. 5 (a) shows an original image generated based on the phase signals before the aliasing correction and FIG. 5 (b) shows a color Doppler image generated based on the phase signals unwrapped by the aliasing correction. As FIGS. 5 (a) and (b), the color Doppler image can be displayed with a more satisfactory image quality by generating the color Doppler image based on the phase signals corrected satisfactorily and stably by the global aliasing correction.

That is, the ultrasonic diagnostic apparatus 1 as mentioned above is an apparatus which performs an aliasing correction of phase signals which is color Doppler image data by a global two-dimensional phase unwrapping processing, and generates and displays a color Doppler image for displaying from the color Doppler image data including the phase signals after the aliasing correction. More specifically, the unwrapped phase signals can be calculated by a series of processing of calculation of gradients of a two-dimensional phase distribution, a discrete cosine transformation, a filter operation on a frequency axis and an inverse cosine transformation. By the unwrapping method under the series of processing mentioned above, a two-dimensional and global solution which minimizes square errors can be obtained as outputs. In addition, the unwrapped phase signals can be obtained in a sequential way by the least squares method using on a phase distribution weighted depending on parameters such as power signal values in the color Doppler image data.

(Effect)

Since the ultrasonic diagnostic apparatus 1 as mentioned above is configured to perform the unwrap processing with regard to the whole of space by a least squares method, the ultrasonic diagnostic apparatus 1 is robust to noise. That is, since the unwrap processing is not a local processing as conventional but a global processing in the ultrasonic diagnostic apparatus 1, the unwrap processing can be performed with robustness even if a change between adjacent phases is large due to influence of noise or there are lots of residues. Further, an influence of data at each position with an improper phase value and/or velocity value due to the influence of noise can be reduced by weighting with a weight determined depending on a parameter such as an amount of phase change, a power value, a dispersion value and a velocity value. Consequently, it is possible to display a color Doppler image without aliasing even if a velocity signal takes a value in a velocity range not less than an aliasing value.

(Modification)

Note that, in the case of measuring a three-dimensional blood flow velocity distribution by ultrasound waves, an aliasing correction processing can be performed by two-dimensional or three-dimensional phase unwrap processing of phase signals φ indicating a three-dimensional blood flow phase distribution. Consequently, a three-dimensional blood flow velocity distribution can be displayed up to a flow velocity range not less than an aliasing velocity.

What is claimed is:

1. An ultrasonic diagnostic apparatus to perform a global aliasing corrections comprising:
    a data acquisition unit configured to acquire phase signals as Doppler data from a moving object within an object by transmitting and receiving ultrasonic waves to and from the object;
    a correction unit configured to perform global aliasing correction processing of the phase signals acquired from the object based on a continuity in a two-dimensionally phase change, the global aliasing correction processing applied to an entirety of a predetermined two-dimensional space as a whole; and
    a display unit configured to display phase signals after the aliasing correction processing,
    wherein the correction unit performs the global aliasing correction processing with a weighted least squares method so as to minimize a square error between signals derived by wrapping gradients in a two-dimensional distribution of the phase signals acquired from the object and gradients in a two-dimensional distribution of phase signals after the global aliasing correction processing with using weights determined according to at least one of power signals of the moving object, dispersion signals of the moving object, velocity signals of the moving object, or gradients of the phase signals acquired from the object.

2. An ultrasonic diagnostic apparatus of claim 1,
    wherein said data acquisition unit configured to acquire three-dimensional phase signals and said correction unit is configured to perform the global aliasing correction processing of the three-dimensional phase signals based on a continuity in a two-dimensionally or three-dimensionally phase change.

3. An ultrasonic diagnostic apparatus of claim 1,
    wherein said correction unit is configured to perform the aliasing correction processing using a property that signals derived by wrapping gradients in a two-dimensional distribution of the phase signals acquired from the object and gradients in a two-dimensional distribution of phase signals after the aliasing correction processing are mutually equal.

4. An ultrasonic diagnostic apparatus of claim 1,
    wherein the correction unit is configured to perform global aliasing correction processing of the phase signals acquired from the object based on a continuity in a two-dimensionally phase change by calculating surface integral of the phase signals acquired from the object for the predetermined two-dimensional space as a whole.

5. An ultrasonic diagnostic apparatus of claim 1,
    wherein the correction unit is configured to perform the global aliasing correction processing of the phase signals acquired from the object based on a continuity in a two-dimensionally phase change without performing local aliasing correction processing which includes selecting a route such that residues are avoided such that the global aliasing correction processing is applied to the predetermined two-dimensional space as a whole, the residues being points in a two-dimensional space on each of which a round integration value of gradient of a phase is not zero.

6. A data processing program for an ultrasonic diagnostic apparatus to perform a global aliasing correction, the program causing a computer to function as:
   a correction unit configured to acquire phase signals acquired from a moving object within an object by transmitting and receiving ultrasonic waves to and from the object, and configured to perform global aliasing correction processing of the phase signals acquired from the object based on a continuity in a two-dimensionally phase change, the global aliasing correction processing applied to an entirety of a predetermined two-dimensional space as a whole; and
   an image data generating unit configured to generate image data for displaying using phase signals after the aliasing correction processing,
   wherein the correction unit performs the global aliasing correction processing with a weighted least squares method so as to minimize a square error between signals derived by wrapping gradients in a two-dimensional distribution of the phase signals acquired from the object and gradients in a two-dimensional distribution of phase signals after the global aliasing correction processing with using weights determined according to at least one of power signals of the moving object, dispersion signals of the moving object, velocity signals of the moving object, or gradients of the phase signals acquired from the object.

7. An ultrasonic diagnostic method to perform a global aliasing correction comprising:
   acquiring phase signals as Doppler data from a moving object within an object by transmitting and receiving ultrasonic waves to and from the object through an ultrasonic probe;
   performing global aliasing correction processing of the phase signals based on a continuity in a two-dimensionally phase change, the global aliasing correction processing applied to an entirety of a predetermined two-dimensional space as a whole; and
   displaying, on a display, phase signals after the aliasing correction processing,
   wherein the global aliasing correction processing is performed with a weighted least squares method so as to minimize a square error between signals derived by wrapping gradients in a two-dimensional distribution of the phase signals acquired from the object and gradients in a two-dimensional distribution of phase signals after the global aliasing correction processing with using weights determined according to at least one of power signals of the moving object, dispersion signals of the moving object, velocity signals of the moving object, or gradients of the phase signals acquired from the object.

* * * * *